United States Patent
Avitsian

(10) Patent No.: US 11,517,692 B2
(45) Date of Patent: Dec. 6, 2022

(54) VENTILATOR CONDUIT FOR REVERSIBLE AIRWAY DEVICE

(71) Applicant: THE CLEVELAND CLINIC FOUNDATION, Cleveland, OH (US)

(72) Inventor: Rafi Avitsian, Solon, OH (US)

(73) Assignee: THE CLEVELAND CLINIC FOUNDATION, Cleveland, OH (US)

(*) Notice: Subject to any disclaimer, the term of this patent is extended or adjusted under 35 U.S.C. 154(b) by 1192 days.

(21) Appl. No.: 15/764,108

(22) PCT Filed: Sep. 30, 2016

(86) PCT No.: PCT/US2016/054647
§ 371 (c)(1),
(2) Date: Jun. 26, 2018

(87) PCT Pub. No.: WO2017/059188
PCT Pub. Date: Apr. 6, 2017

(65) Prior Publication Data
US 2021/0290878 A1  Sep. 23, 2021

Related U.S. Application Data

(60) Provisional application No. 62/235,792, filed on Oct. 1, 2015.

(51) Int. Cl.
*A61M 16/04* (2006.01)
*B29D 22/02* (2006.01)
(Continued)

(52) U.S. Cl.
CPC ........ *A61M 16/0434* (2013.01); *A61M 16/04* (2013.01); *A61M 16/0409* (2014.02);
(Continued)

(58) Field of Classification Search
CPC .......... A61M 16/0434; A61M 16/0488; A61M 16/0463; A61M 16/04; A61M 16/0409;
(Continued)

(56) References Cited

U.S. PATENT DOCUMENTS

2001/0050082 A1* 12/2001 Christopher ...... A61M 16/0409
128/207.15
2006/0263145 A1* 11/2006 Pal ............................ A61F 2/95
403/1

(Continued)

FOREIGN PATENT DOCUMENTS

CN    102917747 A  *  2/2013 ........ A61M 16/0493
CN    209575465 U  *  11/2019
(Continued)

OTHER PUBLICATIONS

M. R. Hernandez and et al., "Evolution of the Extraglottic Airway: A Review of Its History, Applications, and Practical Tips for Success", International Research Society, Feb. 2012 • vol. 114 • No. 2, www.anesthesia-analgesia.org (Year: 2012).*

*Primary Examiner* — Douglas Kay
(74) *Attorney, Agent, or Firm* — Tarolli, Sundheim, Covell & Tummino LLP

(57) ABSTRACT

A ventilator conduit for a reversible airway device (RAD) is provided. The RAD can include a supra-glottic support member connected to a tubular guide (TG) having oppositely disposed proximal and distal end portions and TG lumen, which extends between the ends and is defined by an inner surface. The RAD can be physically free of an endotracheal tube. The ventilator conduit can include a hollow tube having first and second ends, and a ventilator conduit lumen extending between the ends. The first and second ends can be adapted for connection to a ventilator circuit and insertion into the TG lumen, respectively. At least the second end of the hollow tube can be sized and dimensioned so that, (Continued)

upon insertion into the TG, an outer surface of the second end is brought into direct contact with a portion of the inner surface to form an air-tight seal therebetween.

15 Claims, 11 Drawing Sheets

(51) Int. Cl.
  *B29D 99/00* (2010.01)
  *A61J 15/00* (2006.01)
(52) U.S. Cl.
  CPC .... *A61M 16/0463* (2013.01); *A61M 16/0488* (2013.01); *B29D 22/02* (2013.01); *B29D 99/0085* (2013.01); *A61J 15/0049* (2013.01)
(58) Field of Classification Search
  CPC ........... B29C 45/14418; A61J 15/0049; B29D 99/0085
  See application file for complete search history.

(56) References Cited

U.S. PATENT DOCUMENTS

| | | | | |
|---|---|---|---|---|
| 2014/0096766 | A1* | 4/2014 | Avitsian | A61B 1/267 |
| | | | | 128/200.26 |
| 2014/0326238 | A1* | 11/2014 | Spandorfer | A61M 16/14 |
| | | | | 128/203.14 |
| 2018/0214160 | A1* | 8/2018 | Hoskins | A61B 17/135 |

FOREIGN PATENT DOCUMENTS

| | | | | |
|---|---|---|---|---|
| WO | WO-2004043527 A2 * | 5/2004 | ........ | A61M 16/0445 |
| WO | WO-2013141076 A1 * | 9/2013 | ........ | A61M 16/0465 |

* cited by examiner

VENTILATOR CONDUIT FOR REVERSIBLE AIRWAY DEVICE

RELATED APPLICATION

This application claims the benefit of U.S. Provisional Patent Application Ser. No. 62/235,792, filed Oct. 1, 2015, the entirety of which is hereby incorporated by reference for all purposes.

TECHNICAL FIELD

The present disclosure relates generally to the field of anesthesiology and, more particularly, to a ventilator conduit for a reversible airway device that permits use of the reversible airway device as a supra-glottic airway without the need to preload the reversible airway device with an endotracheal tube.

BACKGROUND

Airway devices are widely used in hospital surgical environments to provide respiratory assistance and ventilate patients during medical procedures. While there are a multitude of airway devices currently on the market, one popular airway device is an endotracheal tube and another is a supra-glottic support device, such as a laryngeal mask airway (LMA). While the use of these devices is widespread, there are disadvantages associated with each of these devices.

Endotracheal tubes, for example, are used to ventilate patients requiring anesthesia and/or respiratory assistance. An example of a conventional endotracheal tube is a plastic tube, which is inserted into a subject's mouth or nasal passageway, passed down the trachea through the vocal cords, and lodged in the trachea proximal (or above) the lungs. The endotracheal tube may have a cuff or balloon portion surrounding the circumference of the endotracheal tube near the distal end that rests in the subject's trachea. After the endotracheal tube has been inserted properly, the cuff may be inflated to seal against the wall of the trachea. Once sealed, positive pressure ventilation may be used to provide respiratory assistance and, if desired, anesthesia or other gas, gas mix, etc., to the patient though the endotracheal tube via a ventilator. The cuff provides a seal that tends to block liquids and solids from passing along the outside of the endotracheal tube between the tube and the trachea wall and entering the subject's lungs.

A supraglottic airway typically includes a hollow tube (sometimes referred to as a tubular guide, tube or guide) and a laryngeal mask. The laryngeal mask of the supraglottic airway is intended to fit through the mouth in the oropharynx of a patient and cover the two openings leading, respectively, to the esophagus and the trachea, on the one hand, and blocking the fluid path to and from the esophagus and stomach, on the other hand, thereby providing a fluid path to the trachea and lungs for ventilating the patient. The laryngeal mask may be positioned without requiring a physician to view the glottal opening directly. The laryngeal mask has an inflatable cuff or rim area. Once the laryngeal mask is placed into the subject's mouth, the cuff can be inflated to seal against the walls of the inside of the mouth and, if positioned properly, to block flow to and from the esophagus. A flexible, membranous support material extends from the cuff to form a recessed area, e.g., a space or volume, into which a gas mix can be pumped through the tube or other instrumentality of the supraglottic airway to provide the requisite air and/or anesthesia to the patient. The tube is of relatively large diameter, as compared to the usually relatively narrower diameter passage of a conventional endotracheal tube, and such relatively large diameter facilitates gas mix and exhalant flow with relatively minimal interference, pressure drop, etc. The support material supports the cuff from the tube. Thus, the supraglottic airway can be used to supply a gas mix to the recessed area and from there to the trachea.

In patients that require ventilation with an airway device (e.g., critically ill or injured subjects), it is important to maintain a continuous airway. In such patients, if ventilation begins with a supra-glottic support device (e.g., a LMA) and intubation subsequently becomes necessary, the supra-glottic support device must be removed from the patient so that an endotracheal tube can be placed. Doing so, however, requires that the patient's airway be temporarily disrupted while also increasing the risk that the patient's airway may not be recovered. Additionally, placing an endotracheal tube requires the skill of an experienced medical professional, who may not be present in all circumstances in which unexpected intubation is required.

Reversible airway devices have been developed to address these drawbacks. Examples of such devices are disclosed in PCT Application Serial No. PCT/US15/41870 to Avitsian et al., U.S. patent application Ser. No. 14/048,343 to Avitsian et al., and U.S. patent application Ser. No. 14/795,932 to Avitsian et al. The reversible airway devices disclosed by Avitsian et al. generally comprise a tubular guide, a laryngeal mask, and an endotracheal tube slidably disposed within the tubular guide. The presence of the endotracheal tube facilitates transition between supra-glottic and infra-glottic support that does not risk disconnection or loss of the patient's airway during ventilation. In some instances, such as an emergency, the need may arise to provide a supra-glottic airway and connection to a ventilator. In such instances, however, the presence of the endotracheal tube in the reversible airway devices may hinder or prevent the ability of medical personnel to rapidly establish the supra-glottic airway.

SUMMARY

The present disclosure relates generally to the field of anesthesiology and, more particularly, to a ventilator conduit for a reversible airway device that permits use of the reversible airway device as a supra-glottic airway without the need to preload the reversible airway device with an endotracheal tube.

One aspect of the present disclosure relates to a ventilator conduit for a reversible airway device. The reversible airway device can comprise a supra-glottic support member connected to a tubular guide. The tubular guide can include oppositely disposed proximal and distal end portions and a tubular guide lumen, which extends between the proximal and distal end portions and is defined by an inner surface. The reversible airway device can be physically free of an endotracheal tube. The ventilator conduit can comprise a hollow tube including a first end, a second, end, and a ventilator conduit lumen extending between the first and second ends. The first end can be adapted for connection to a ventilator circuit. The second end can be adapted for insertion into the tubular guide lumen of the reversible airway device. At least the second end of the hollow tube can be sized and dimensioned so that, upon insertion of the hollow tube into the tubular guide, an outer surface of the second end is brought into direct contact with a portion of the inner surface of the tubular guide to form an air-tight seal therebetween.

Another aspect of the present disclosure relates to a system for ventilating a patient. The system can comprise a reversible airway device including a tubular guide and a ventilator conduit partly disposed within the tubular guide. The reversible airway device can further comprise a supraglottic support member connected to the tubular guide. The tubular guide can include oppositely disposed proximal and distal end portions and a tubular guide lumen, which extends between the proximal and distal end portions and is defined by an inner surface. The reversible airway device can be physically free of an endotracheal tube. The ventilator conduit can comprise a hollow tube including a first end, a second, end, and a ventilator conduit lumen extending between the first and second ends. The first end can be adapted for connection to a ventilator circuit. The second end can be adapted for insertion into the tubular guide lumen of the reversible airway device. At least the second end of the hollow tube can be sized and dimensioned so that, upon insertion of the hollow tube into the tubular guide, an outer surface of the second end is brought into direct contact with a portion of the inner surface of the tubular guide to form an air-tight seal therebetween.

Another aspect of the present disclosure can include a method for ventilating a subject. One step of the method can include inserting a reversible airway device, without an endotracheal tube associated therewith, into an airway of the subject. The reversible airway device can comprise a supraglottic support member connected to a tubular guide. Next, a ventilator conduit can be inserted into the tubular guide so that an outer surface of a second end of the ventilator conduit is brought into direct contact with a portion of an inner surface of the tubular guide to form an air-tight seal therebetween. A first end of the ventilator conduit can then be connected to a ventilator circuit.

Another aspect of the present disclosure relates to a method for ventilating a subject that is intubated with an endotracheal tube of a reversible airway device. One step of the method can include detaching the endotracheal tube from the reversible airway device. Next, a ventilator conduit can be inserted into the tubular guide so that an outer surface of a second end of the ventilator conduit is brought into direct contact with a portion of an inner surface of the tubular guide to form an air-tight seal therebetween. A first end of the ventilator conduit can then be connected to a ventilator circuit.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1A:
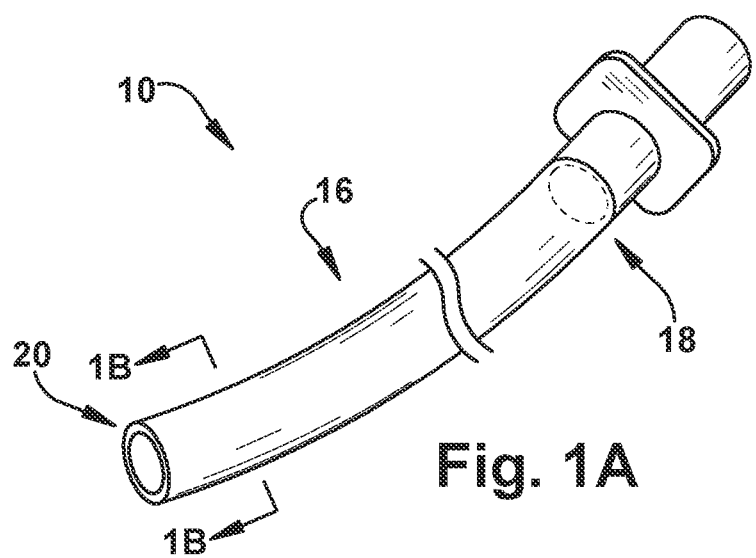
FIG. 1A is a schematic illustration of a ventilator conduit for a reversible airway device constructed in accordance with one aspect of the present disclosure.

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the terms "ventilating" or "ventilate" can refer to providing breathable air or oxygen, for example, and removing gas, etc., e.g., exhalant exhaled by a subject, and providing anesthesia and/or other materials to and/or from the lungs of a subject. The terms can also have the usual meaning as used in the field of medicine. The various gases, e.g., oxygen, air, anesthesia, etc., alone or in combination sometimes are referred to below collectively as a gas mixture.

As used herein, the terms "subject" and "patient" can be used interchangeably and refer to any warm-blooded organism including, but not limited to, human beings, pigs, rats, mice, dogs, goats, sheep, horses, monkeys, apes, rabbits, cattle, etc.

Overview

Figure 1B:
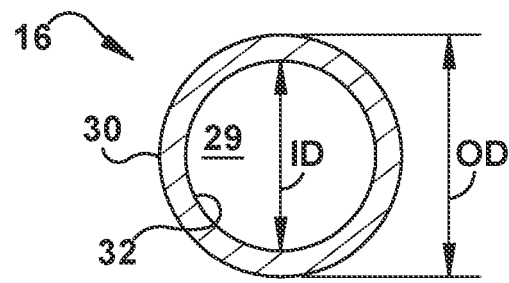
FIG. 1B is a cross-sectional view taken along Line 1B-1B in FIG. 1A.
Figure 1C:
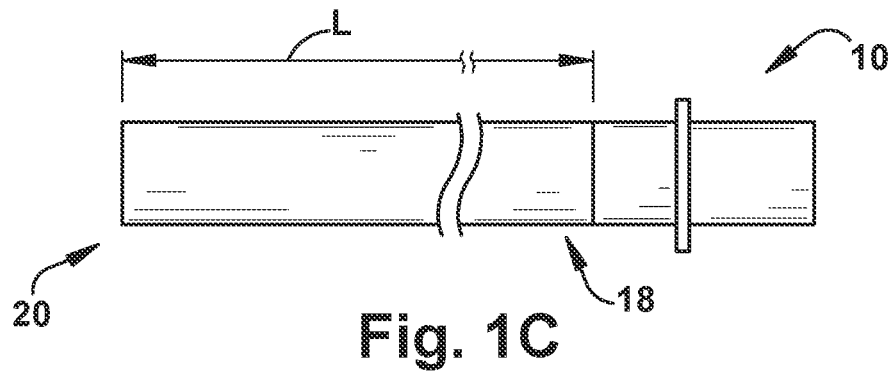
FIG. 1C is a side view of the ventilator conduit shown in FIG. 1A.
Figure 2:
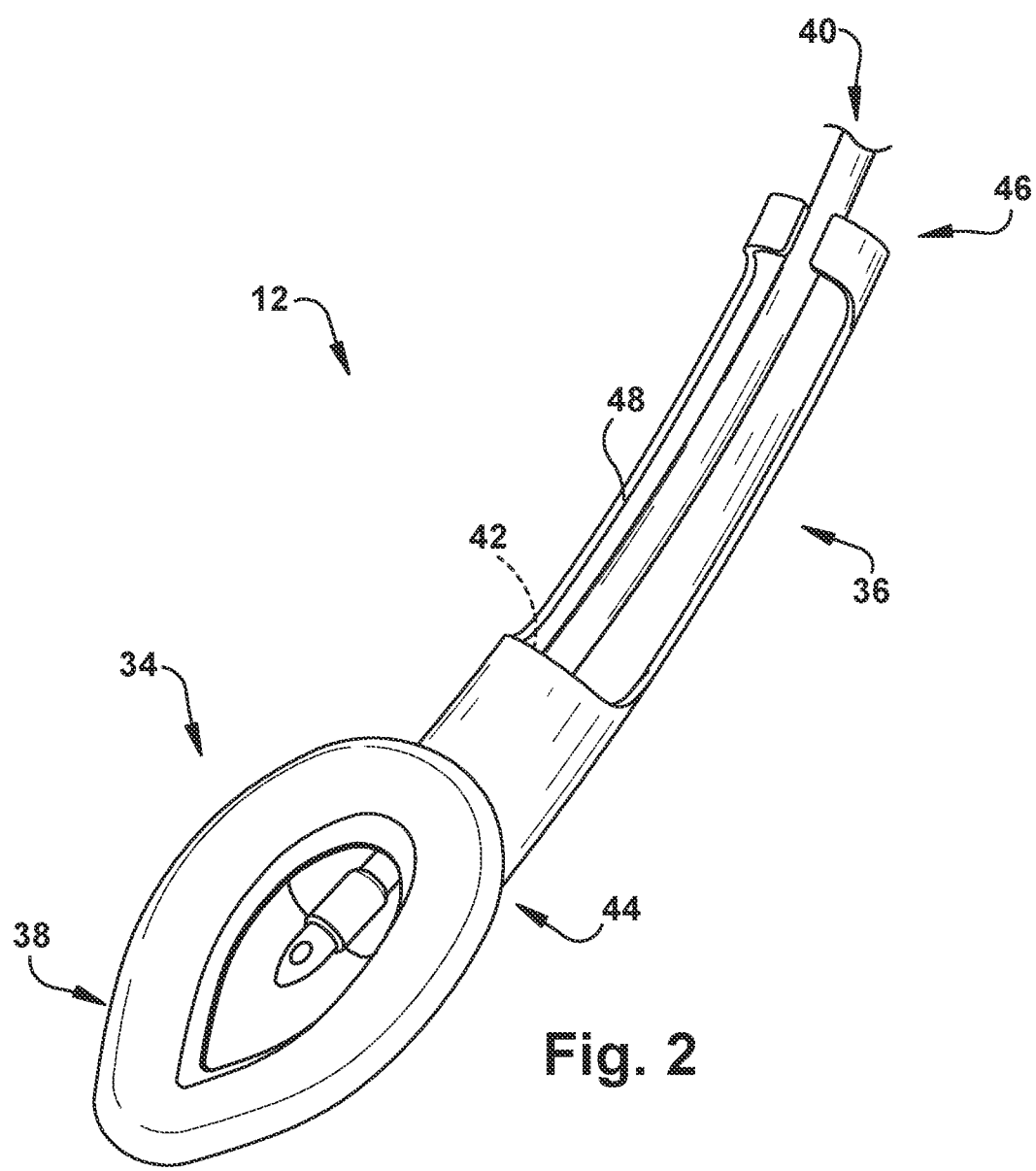
FIG. 2 is a schematic illustration of a reversible airway device.

The present disclosure relates generally to the field of anesthesiology and, more particularly, to a ventilator conduit for a reversible airway device that permits use of the reversible airway device as a supra-glottic airway without the need to preload the reversible airway device with an endotracheal tube. As representative of one aspect of the present disclosure, FIGS. 1A-C illustrate a ventilator conduit 10 for a reversible airway device 12 (FIG. 2). The ventilator conduit 10 (FIGS. 1A-C) is sized and dimensioned for use with any one or combination of the reversible airway devices as disclosed in PCT Application Serial No. PCT/US15/41870 to Avitsian et al., U.S. patent application Ser. No. 14/048,343 to Avitsian et al., and U.S. patent application Ser. No. 14/795,932 to Avitsian et al. ("the '932 application"). Advantageously, the ventilator conduit 10, when disposed within a reversible airway device 12, provides medical personnel with the ability to use the combination device as a supra-glottic airway without the need to preload an endotracheal tube (not shown).

Devices and Systems

Referring to FIGS. 1A-C, one aspect of the present disclosure can include a ventilator conduit 10 for insertion into a reversible airway device 12 (FIG. 2). One example of a reversible airway device 12 is shown in FIG. 2. The reversible airway device 12 can include a supra-glottic airway support 34 (e.g., comprising a tubular guide 36 and a laryngeal mask 38), an endotracheal tube 40, and a sealing mechanism (not shown). The tubular guide 36 can include a first passageway 42 that is defined by an inner surface 48 of the tubular guide. The first passageway 42 can extend between a distal end portion 44 and a proximal end portion 46 of the tubular guide 36. The first passageway 42 is sized and dimensioned to receive the endotracheal tube 40. Other features that may be included as part of the reversible airway device 12, all of which are incorporated herein by reference, are disclosed in the '932 application as well as the other aforementioned patent applications to Avitsian et al.

In another aspect, the ventilator conduit 10 (FIGS. 1A-C and FIG. 5) can comprise a hollow tube 16 with a ventilator conduit lumen 29 extending between first and second ends 18 and 20 thereof. The proximal end 18 can be adapted for attachment to a standard ventilation circuit (not shown) for ventilation (e.g., a 22 mm ventilation circuit). The second end 20 can be sized and dimensioned for insertion into a tubular guide 36 (FIG. 2) of a reversible airway device 12. The hollow tube 16 (FIG. 1B) can be defined by an outer surface 30 and an inner surface 32. As shown in FIG. 1B, the hollow tube 16 also includes an inner diameter ID and an outer diameter OD, which is greater than the inner diameter ID. At least the second end 20 of the hollow tube 16 is sized and dimensioned so that, upon insertion of the hollow tube into the tubular guide 36 of a reversible airway device 12, the outer surface 30 of the second end is brought into direct contact with a portion of the inner surface 48 of the tubular guide to form an air-tight seal therebetween. In some instances, the outer diameter OD can be equal to, or about equal to (e.g., less than) an inner diameter of the tubular guide 36 so that the outer surface 30 can be brought into direct contact with the inner surface 48 upon insertion of the hollow tube 16 into the tubular guide. In other instances, only the outer surface 30 of the second end 20 is brought into direct contact with the portion of the inner surface 48 of the tubular guide 36 upon insertion of the hollow tube 16 into the tubular guide.

As shown in FIG. 1C, the ventilator conduit 10 can have a length L that extends between the first and second ends 18 and 20. The length L of the ventilator conduit 10 should be at least the length of the tubular guide 36 comprising the reversible airway device 12. In some instances, the length L of the ventilator conduit 10 is such that a length of the first end 18 of the ventilator conduit extends axially beyond the proximal end portion 46 of the tubular guide when the ventilator conduit is disposed within the tubular guide. Advantageously, the length at the first end 18 permits connection of the first end 18 of the ventilator conduit 10 to a ventilation circuit. The caliber of the ventilator conduit 10 will depend on the size of the reversible airway device 12, but will at least be sized and dimensioned to snugly fit inside the tubular guide 36 of the reversible airway device. For example, the outer diameter OD of the ventilator tube 10 can be sufficiently sized to establish a seal against the inner surface 48 of the tubular guide 36 (or a portion of the laryngeal mask 38) of the reversible airway device 12.

Figure 6:
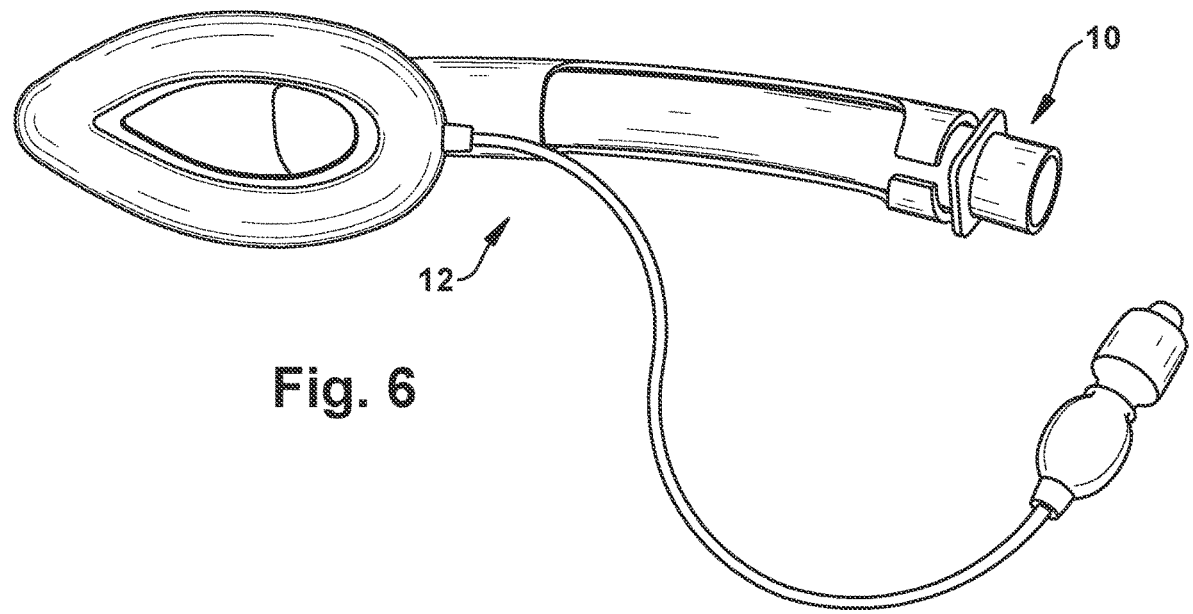
FIG. 6 is an image of the ventilator conduit in FIG. 5 inserted within the reversible airway device of FIG. 5.

In another aspect, at least the second end 20 of the ventilator conduit 10 is sized and dimensioned to form a seal between an outer surface 30 thereof and the inner surface 48 defining the first passageway 42 of the tubular guide 36 (or the laryngeal mask 38). When the ventilator conduit 10 is disposed within the tubular guide 36 (FIG. 6) and connected to a ventilator circuit (or any source of positive pressure or mechanical ventilation), this permits a steady, uninterrupted flow of a gas through the ventilator conduit.

In another aspect, the ventilator conduit 10 can also include a notch or diaphragm (not shown) at the first end 18 to facilitate handling, such as grabbing, pulling or pushing to place the ventilator conduit within the tubular guide 36.

Another aspect of the present disclosure can include a ventilator conduit 10' as shown in FIGS. 3A-H. The ventilator conduit 10' can be identically constructed as the ventilator conduit 10 shown in FIGS. 1A-C, except where described below. For example, The ventilator conduit 10' can be identically constructed as the ventilator conduit 10 shown in FIGS. 1A-C, except that the ventilator conduit of FIGS. 3A-H can include a sealing member 50 that is physically associated (e.g., connected to or formed from) with a portion (e.g., only the second end 20 of the hollow tube) of the hollow tube 16. As discussed below, the sealing member 50 advantageously provides a mechanism for creating an air-tight seal between the ventilator conduit 10' and the tubular guide 36 of the reversible airway device 12.

Figure 3A:
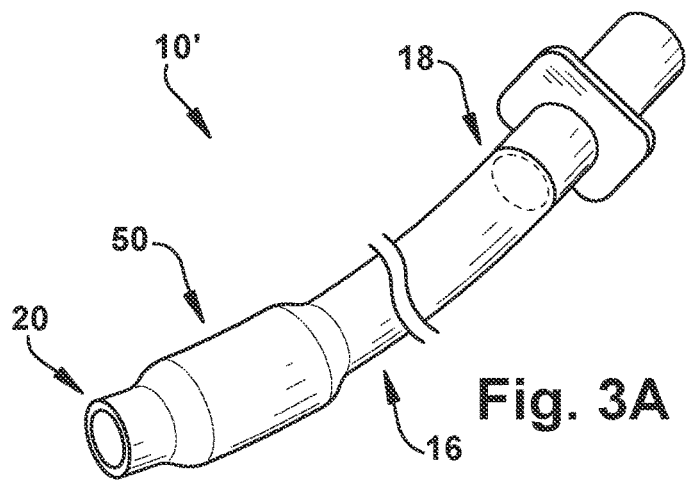
FIG. 3A is a schematic illustration of a ventilator conduit for a reversible airway device constructed in accordance with another aspect of the present disclosure.
Figure 3B:
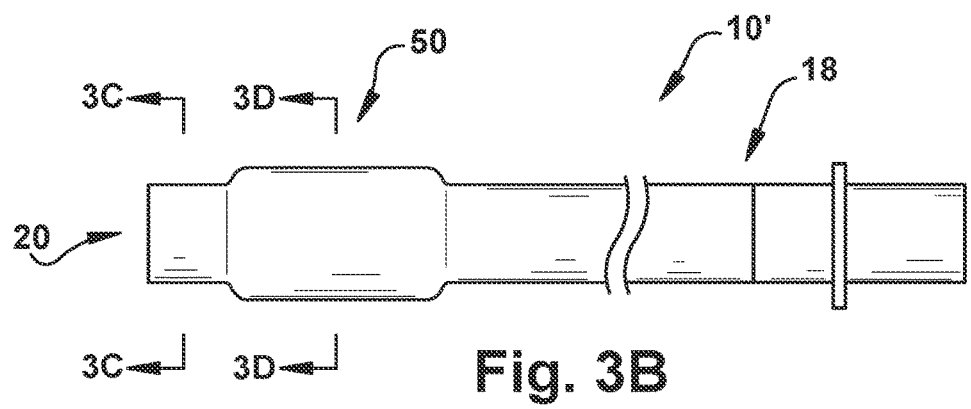
FIG. 3B is a side view of the ventilator conduit shown in FIG. 3A.
Figure 3C:
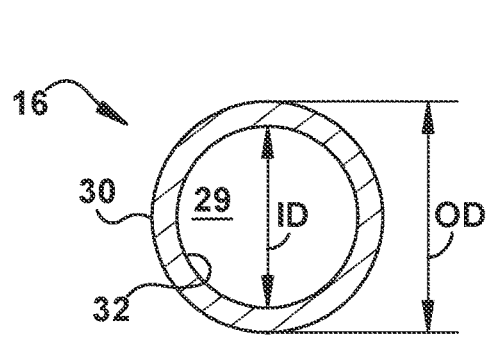
FIG. 3C is a cross-sectional view taken along Line 3C-3C in FIG. 3B.
Figure 3D:
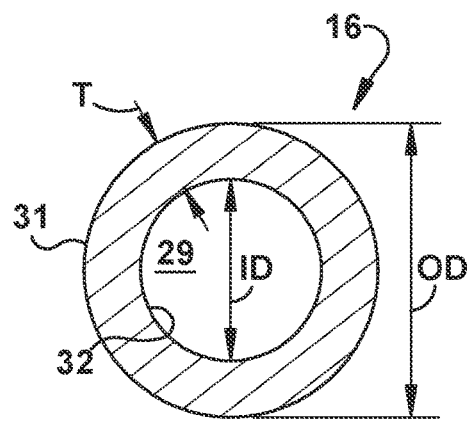
FIG. 3D is a cross-sectional view taken along Line 3D-3D in FIG. 3B.
Figure 3E:
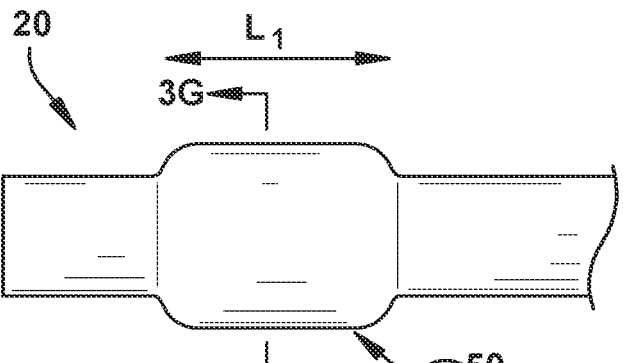
FIG. 3E is a schematic illustration showing an enlarged view of a sealing member of the ventilator conduit in FIG. 3A having a first shape.

In some instances, the sealing member 50 can comprise a deformable or semi-solid material (e.g., viscoelastic, elastic, liquid or semi liquid, such as a gel) whose shape can be altered by applying stress or pressure to the material. For example, the sealing member 50, by virtue of the deformable or semi-solid material, can be compressed, shortened, expanded, or elongated, either axially, radially or obliquely. The sealing member 50 can be disposed about (e.g., circumferentially disposed about, e.g., layered) or incorporated into a portion (e.g., the second end 20 or only the second end) of the hollow tube 16. FIGS. 3A-D illustrate one example of the sealing member 50 wherein the sealing member is comprised of the same material from which the rest of the hollow tube 16 is formed. In this example, the sealing member 50 has an increased thickness T relative to the remainder of the hollow tube (FIG. 3D). It should be appreciated that the material used to form the sealing member 50 may be different than the material that forms the remainder of the hollow tube 16. It will also be appreciated that the deformable material can be directly attached to, and circumferentially envelop, a portion of the outer surface 30 of the hollow tube 16 (e.g., so that the second end 20 of the ventilator conduit 10 has a multi-layer configuration).

Figure 3F:
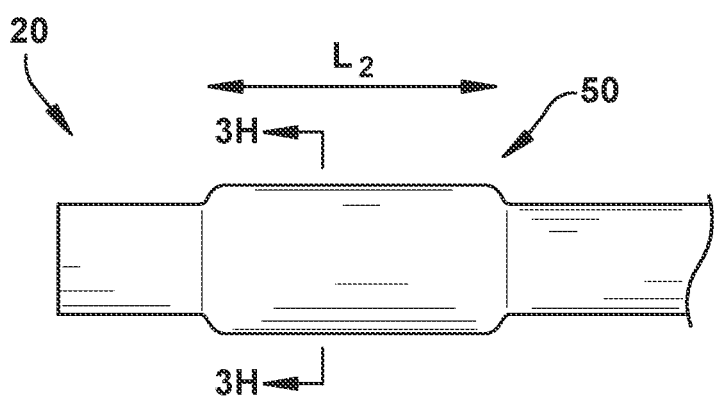
FIG. 3F is a schematic illustration showing the sealing member in FIG. 3E having a different second shape.
Figure 3G:
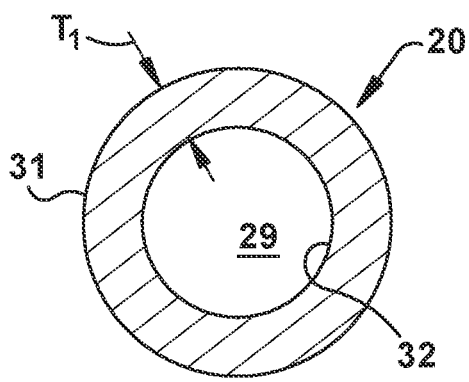
FIG. 3G is a cross-sectional view taken along Line 3G-3G in FIG. 3E.
Figure 3H:
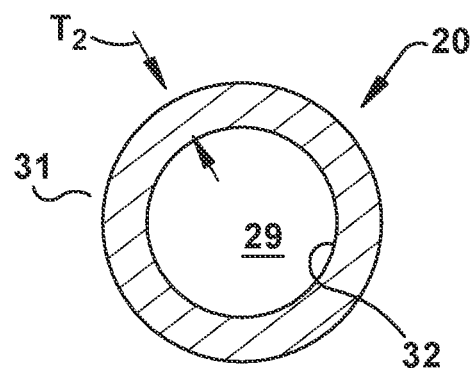
FIG. 3H is a cross-sectional view taken along Line 3H-3H in FIG. 3F.

FIGS. 3E-H illustrate deformation of the sealing member 50 upon insertion of the ventilator conduit 10' into a reversible airway device 12. Prior to insertion, the sealing member 50 has a first shape defined by a first length L1 and a first thickness T1 (FIG. 3G). When the ventilator conduit 10' is inserted into the reversible airway device 12, the first shape changes or transitions into a second shape (by virtue of the deformable material) such that the second shape creates or facilities creation of an air-tight seal between the inner surface 48 of the tubular guide 36 and an outer surface 31 of the sealing member 50. As can be seen in FIGS. 3F and 3H, insertion of the ventilator conduit 10' into the tubular guide 36 simultaneously causes the sealing member 50 to obtain the second shape, which is defined by a second length L2 that is greater than the first length L1 and a second thickness T2 that is less than the first thickness T1. Advantageously, construction of the ventilator tube 10' with the deformable material not only provides an effective way of establishing an air-tight seal between the inner surface 48 of the tubular guide 36 and the outer surface 31 of the sealing member 50, but also provides a mechanism for placing and extracting the ventilator conduit with minimal effort.

Figure 4:
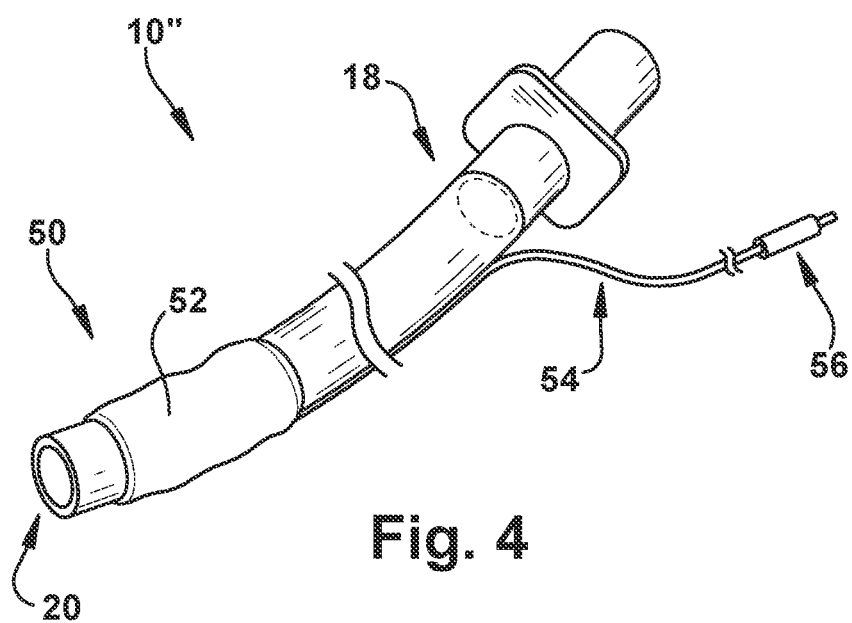
FIG. 4 is a schematic illustration of a ventilator conduit for a reversible airway device constructed in accordance with another aspect of the present disclosure.
Figure 5:
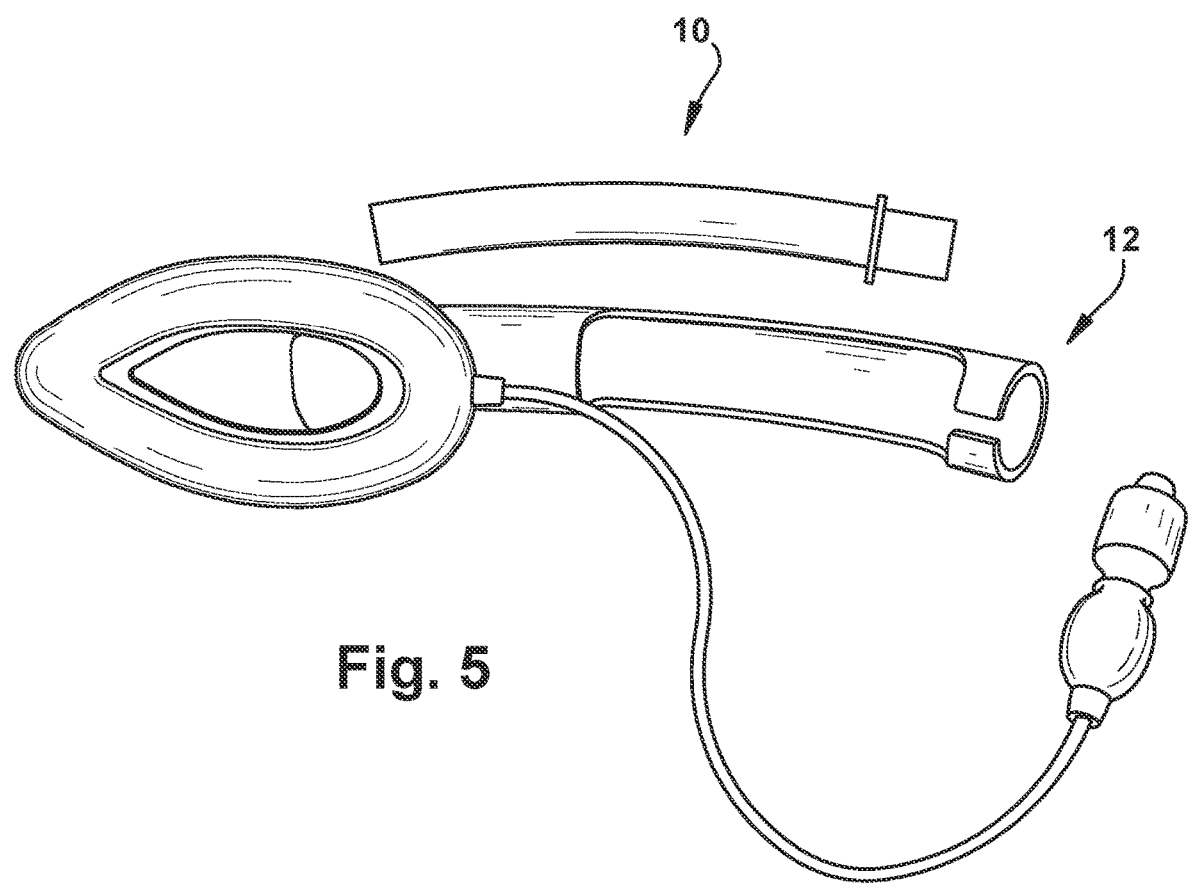
FIG. 5 is an image of the ventilator conduit in FIG. 1A and the reversible airway device in FIG. 2.
Figure 7:
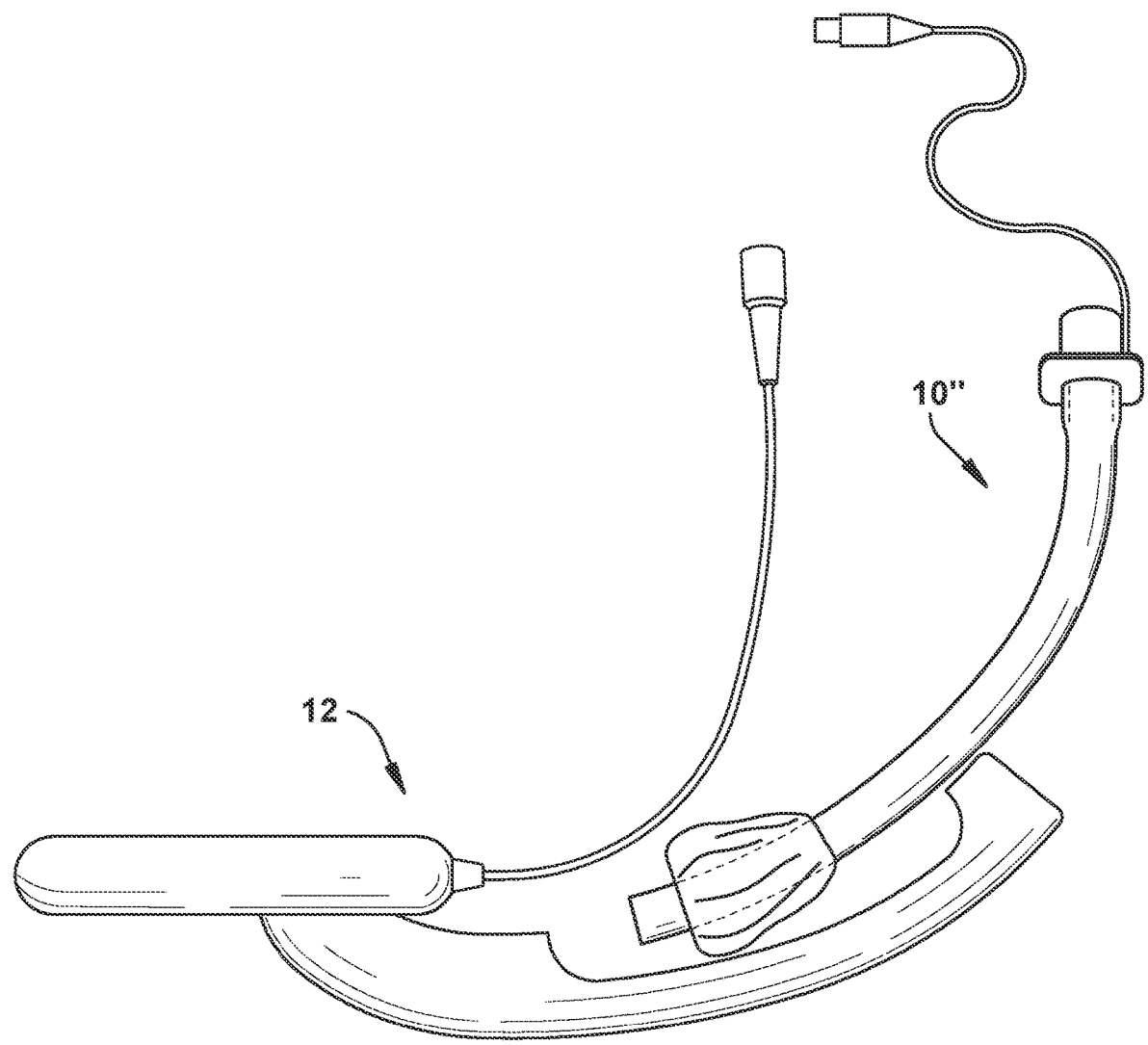
FIG. 7 is an image of the ventilator conduit in FIG. 4 and the reversible airway device in FIG. 2.
Figure 8:
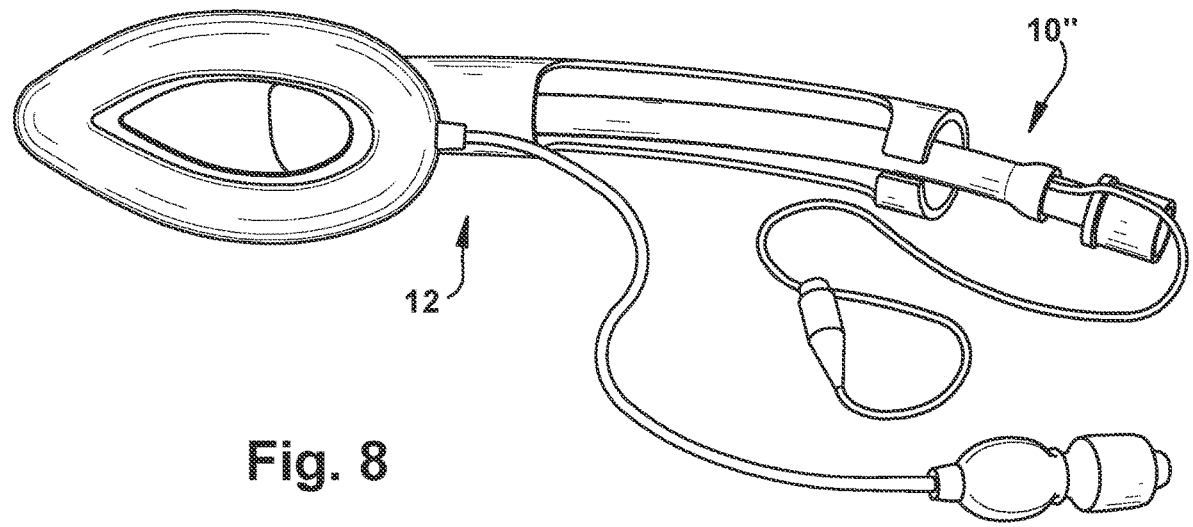
FIG. 8 is an image of the ventilator conduit in FIG. 7 inserted within the reversible airway device of FIG. 7.

In another aspect, the sealing member 50 of a ventilator conduit 10" can comprise an inflatable balloon 52 (FIGS. 4 and 7-8) that is disposed about a portion (e.g., the second end 20 or only the second end) of the hollow tube 16. In some instances, the balloon 52 can be similar or identical to a cuff of an endotracheal tube. In this configuration, the ventilator conduit 10" can additionally include an integral fluid tube 54 having a lumen in fluid communication with a lumen of the balloon 52. The fluid tube 54 can be attached (e.g., at a proximal end 56 thereof) to a fluid source (not shown). The balloon 52 can be selectively inflated to make an air-tight seal between the outer surface thereof and the inner surface 48 of the tubular guide 36 (or the laryngeal mask 38), thereby allowing ventilation when placed in a patient.

Methods

Another aspect of the present disclosure can include methods 58 and 60 (FIGS. 9 and 10, respectively) for ventilating a patient in need thereof. The methods 58 and 60 are illustrated as process flow diagrams with flowchart illustrations. For purposes of simplicity, the methods 58 and 60 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 58 and 60.

Figure 9:
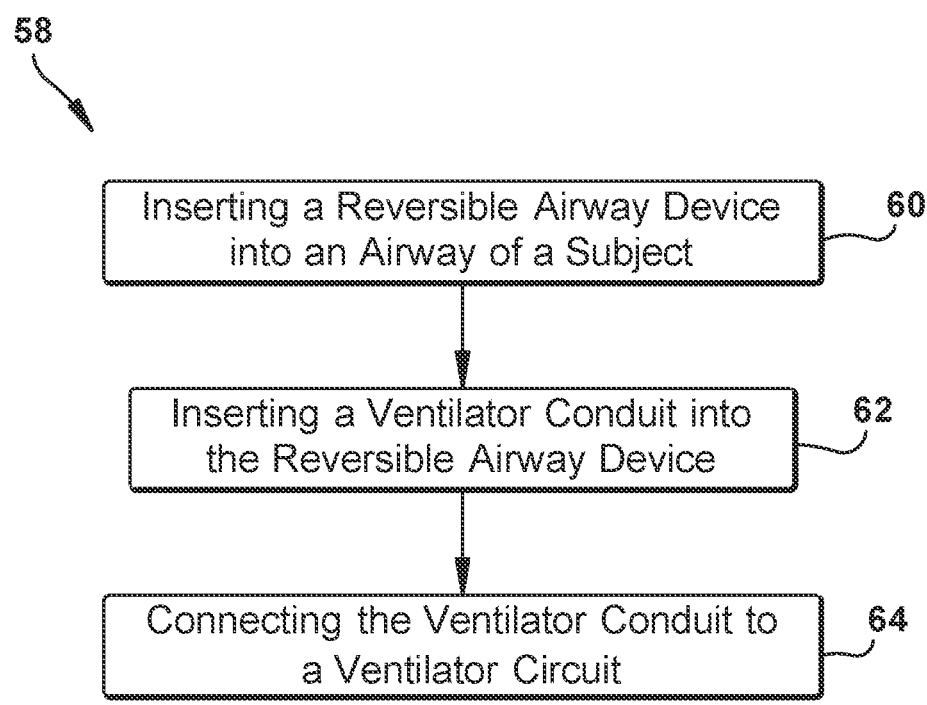
FIG. 9 is a process flow diagram illustrating a method for ventilating a subject according to another aspect of the present disclosure.

In one aspect, FIG. 9 illustrates a method 58 for ventilating a subject comprising the steps of: inserting a reversible airway device into an airway of a subject (Step 60); inserting a ventilator conduit into the reversible airway device (Step 62); and connecting the ventilator conduit to a ventilator circuit (Step 64). Although the method 58 is described below using the ventilator conduit 10 shown in FIGS. 1A-C, it will be appreciated that any of the other ventilator conduits 10' and 10" described herein, or a combination thereof, may be used according to the method 58.

At Step 60, a reversible airway device 12 (e.g., as shown in FIG. 2), without an endotracheal tube 40 associated therewith, can be inserted into the airway of a subject as described, for example, in the '932 application. For example, a medical practitioner or emergency responder can insert the reversible airway device 12 into the subject's airway during an emergency situation to establish a patent airway. Alternatively, if a medical practitioner is simply unsure of the need for endotracheal intubation, the medical practitioner can insert the reversible airway device 12 into the subject's airway.

At Step 62, the ventilator conduit 10 can be inserted into the reversible airway device 12 so that the outer surface 30 of the hollow tube 16 (e.g., located at the second end 20 thereof) is brought into direct contact with a portion of the inner surface 48 of the tubular guide 36 to form an air-tight seal therebetween.

At Step 64, the first end 18 of the ventilator conduit 10 can be connected to a ventilator circuit, which can then be activated to ventilate the subject for a desired period of time. If a medical practitioner is aware of the need to introduce an endotracheal tube 40, the medical practitioner can discontinue operation of the ventilator circuit, disconnect the ventilator conduit 10 therefrom, remove the ventilator conduit from the reversible airway device 12, and then replace the ventilator conduit with an endotracheal tube.

Figure 10:
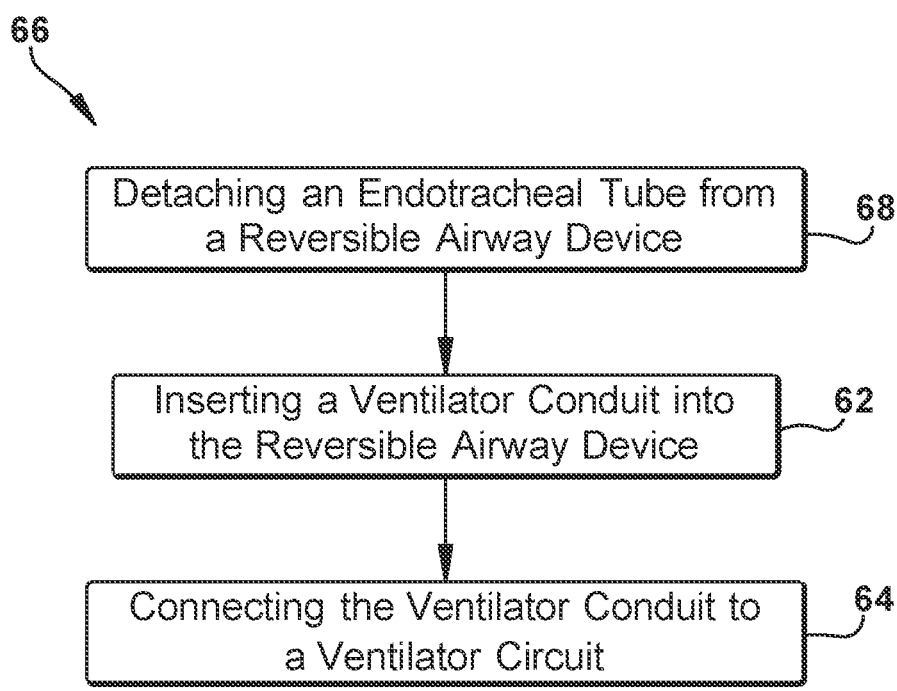
FIG. 10 is a process flow diagram illustrating a method for ventilating a subject that is intubated with an endotracheal tube of a reversible airway device according to another aspect of the present disclosure.

In another aspect, FIG. 10 illustrates a method 66 for ventilating a subject that is intubated with an endotracheal tube 40 of a reversible airway device 12. The method 66 can include the steps of: detaching the endotracheal tube from the reversible airway device (Step 68); inserting a ventilator conduit into the reversible airway device (Step 62); and connecting the ventilator conduit to a ventilator circuit (Step 64). Although the method 58 is described below using the ventilator conduit 10 shown in FIGS. 1A-C, it will be appreciated that any of the other ventilator conduits 10' and 10" described herein, or a combination thereof, may be used according to the method 66.

At Step 68, a subject that is intubated with an endotracheal tube 40 of a reversible airway device 12 can have the endotracheal tube removed or detached therefrom by a medical practitioner, after which it may be necessary to establish a supra-glottic airway for ventilation. In this case, a ventilator conduit 10 can be inserted into the reversible airway device 12 (Step 62) and then connected to a ventilator circuit (Step 64), which can then be activated to ventilate the subject for a desired period of time. If a medical practitioner is aware of the need to re-introduce an endotracheal tube 40, the medical practitioner can discontinue operation of the ventilator circuit, disconnect the ventilator conduit 10 therefrom, remove the ventilator conduit from the reversible airway device 12, and then replace the ventilator conduit with the endotracheal tube.

It should be appreciated that, in some instances, the ventilator conduit 10 can be pre-loaded within the reversible airway device so that the combination device or system (e.g., FIGS. 6 and 8) is ready to be used to establish a supra-glottic airway for ventilation.

From the above description of the present disclosure, those skilled in the art will perceive improvements, changes and modifications. For example, although use of the ventilator conduit 10, 10', and 10" is described above with application to a ventilator circuit or source of positive/mechanical pressure, it will be appreciated that the ventilator conduit, when combined with a reversible airway device 12, can allow a patient to have spontaneous ventilation as well. Such improvements, changes, and modifications are within the skill of those in the art and are intended to be covered by the appended claims. All patents, patent applications, and publication cited herein are incorporated by reference in their entirety.

The following is claimed:

1. A system for ventilating a patient, the system comprising:
    a reversible airway device, the reversible airway device comprising a supra-glottic support member directly connected to an end of a tubular guide, the tubular guide including oppositely disposed proximal and distal end portions and a tubular guide lumen, which extends between the proximal and distal end portions and is defined by an inner surface of the tubular guide, the reversible airway further comprising an endotracheal tube sized and dimensioned to be received in the tubular guide lumen; and
    a ventilator conduit configured to be partly disposed within the tubular guide, the ventilator conduit comprising a hollow tube including a first end, a second end, and a ventilator conduit lumen extending between the first and second ends, the first end being adapted for connection to a ventilator circuit and the second end being adapted for insertion into the tubular guide lumen of the reversible airway device;
    wherein at least the second end of the hollow tube is sized and dimensioned so that an outer surface of the second end directly contacts a portion of the inner surface of the tubular guide when the hollow tube is removably inserted in the tubular guide lumen, an air-tight seal being formed directly between the outer surface of the second end and the inner surface of the tubular guide when the outer surface of the second end directly contacts the inner surface of the tubular guide; and
    wherein the system is configured such that the hollow tube, when inserted in the tubular guide lumen, is removable from the tubular guide lumen and replaceable with the endotracheal tube.

2. The system of claim 1, wherein only the outer surface of the second end is brought into direct contact with the portion of the inner surface of the tubular guide upon insertion of the hollow tube into the tubular guide.

3. The system of claim 1, wherein the hollow tube has a length that is greater than a length of the tubular guide.

4. The system of claim 3, wherein a length of the hollow tube extends beyond the proximal end of the tubular guide.

5. The system of claim 1, further including a sealing member associated with a portion of the hollow tube.

6. The system of claim 5, wherein the sealing member comprises an inflatable balloon disposed circumferentially around a portion of the hollow tube.

7. The system of claim 5, wherein the sealing member comprises a deformable material that is disposed circumferentially around a portion of the hollow tube, the deformable material having a first shape that changes to a second different shape when the hollow tube is inserted into the tubular guide such that the second shape creates an air-tight seal between the inner surface of the tubular guide an outer surface of the sealing member.

8. The system of claim 7, wherein the deformable material is formed from a different material than a material that forms the tubular guide.

9. The system of claim 7, wherein the deformable material is directly attached to, and circumferentially envelops, a portion of the outer surface of the hollow tube.

10. A method for ventilating a subject, the method comprising the steps of:
    providing the system of claim 1;
    inserting the reversible airway device, without an endotracheal tube associated therewith, into an airway of the subject;
    inserting the ventilator conduit into the tubular guide so that the outer surface of the second end of the ventilator conduit is brought into direct contact with a portion of the inner surface of the tubular guide to form an air-tight seal between the outer surface of the second end and the inner surface of the tubular guide; and
    connecting the first end of the ventilator conduit to the ventilator circuit.

11. A method for ventilating a subject that is intubated with an endotracheal tube of a reversible airway device, the method comprising the steps of:
    providing the system of claim 1;
    detaching the endotracheal tube from the reversible airway device;
    inserting the ventilator conduit into the tubular guide so that the outer surface of the second end of the ventilator conduit is brought into direct contact with a portion of the inner surface of the tubular guide to form an air-tight seal between the outer surface of the second end and the inner surface of the tubular guide; and
    connecting the first end of the ventilator conduit to the ventilator circuit.

12. The ventilator conduit of claim 1, wherein a length of the hollow tube is configured such that the second end of the hollow tube is prevented from extending beyond the supra-glottic support member when the hollow tube is inserted into the tubular guide lumen of the reversible airway device.

13. The system of claim 1, wherein the system is configured such that the endotracheal tube, when inserted in the tubular guide lumen, is removable from the tubular guide lumen and replaceable with the ventilator conduit.

14. The system of claim 1, wherein a sealing member is connected to the second end of the hollow tube and forms the portion of the second end of the hollow tube that directly contacts the inner surface of the tubular guide when the hollow tube is removably inserted in the tubular guide lumen.

15. A system for ventilating a patient, the system comprising:
- a reversible airway device, the reversible airway device comprising a supra-glottic support member directly connected to an end of a tubular guide, the tubular guide including oppositely disposed proximal and distal end portions and a tubular guide lumen, which extends between the proximal and distal end portions and is defined by an inner surface of the tubular guide, the reversible airway further comprising an endotracheal tube sized and dimensioned to be received in the tubular guide lumen; and
- a ventilator conduit configured to be partly disposed within the tubular guide, the ventilator conduit including a first end, a second end, and a ventilator conduit lumen extending between the first and second ends, the first end being adapted for connection to a ventilator circuit and the second end being adapted for insertion into the tubular guide lumen of the reversible airway device;

wherein the ventilator conduit includes a sealing member at the second end of the ventilator conduit and adapted to be inserted together with the second end of the ventilator conduit into the tubular guide lumen, the sealing member being sized and dimensioned to directly contact the inner surface of the tubular guide when the ventilator conduit is removably inserted in the tubular guide lumen, an air-tight seal being formed directly between the ventilator conduit and the tubular guide when the sealing member directly contacts the inner surface of the tubular guide; and wherein the system is configured such that the ventilator conduit, when inserted in the tubular guide lumen, is removable from the tubular guide lumen and replaceable with the endotracheal tube.

\* \* \* \* \*